United States Patent [19]

DesMarais

[11] 4,110,276

[45] Aug. 29, 1978

[54] POLYESTER FOAM MATERIALS

[75] Inventor: Thomas A. DesMarais, Norwood, Ohio

[73] Assignee: The Procter & Gamble Company, Cincinnati, Ohio

[21] Appl. No.: 843,606

[22] Filed: Oct. 19, 1977

Related U.S. Application Data

[63] Continuation-in-part of Ser. No. 737,930, Nov. 2, 1976, abandoned.

[51] Int. Cl.$^2$ .................................................. C08J 9/00
[52] U.S. Cl. .................................... 521/123; 521/182; 521/182; 521/189; 521/905
[58] Field of Search ............ 260/2.5 N, 2.5 EP, 75 EP

[56] References Cited

U.S. PATENT DOCUMENTS 3,815,601  11/1974  Schaefer ............................... 128/285

Primary Examiner—M. J. Welsh
Attorney, Agent, or Firm—Monte D. Witte; Fredrick H. Braun; Richard C. Witte

[57] ABSTRACT

Resilient polyester foam materials. Acyl halide, polyol, and polyhydroxy cross-linking agent are reacted in the presence of alkali metal carbonate to prepare the resilient polyester foams. A process similar to that used in the one-shot preparation of polyurethane foams is used. Preferred reactants are adipyl chloride, quadrafunctional polyol based on pentaerythritol, propoxylated pentaerythritol cross-linking agent, and sodium carbonate. The resilient polyester foams find use in products such as catamenial tampons.

30 Claims, No Drawings

POLYESTER FOAM MATERIALS

CROSS-REFERENCE TO RELATED APPLICATION

This is a continuation-in-part of application Ser. No. 737,930, filed Nov. 2, 1976 and now abandoned.

BACKGROUND OF THE INVENTION

1. Field of the Invention

This invention relates generally to polyester foam materials and, more specifically, to resilient polyester foams.

2. Description of the Prior Art

Polyesters may be broadly defined as macromolecular compounds having a plurality of carboxylate ester groups in their skeletal structures. Polyesters, as so defined for use herein, are to be distinguished from other ester-containing polymers (e.g. cellulose esters, polyvinyl esters, and polyacrylates) wherein carboxylate groups are present in substituent entities pendant from the backbone of the polymer. Polyesters have been known to science for many years and have been used in recent years in such diverse applications as coatings, films, fibers, molding and casting compounds, and as intermediates in chemical reactions. Polyester foams based on unsaturated acids and unsaturated monomeric cross-linking materials have also been known and used. Foams made from polyesters whose polymeric structure is not dependent for development on unsaturation within its substituent monomers, however, have received scant if any attention in the past. And the same is specifically true of resilient foams made from such polyesters.

Most polyesters finding use today are linear polymers as opposed to three dimensional polymers. Three dimensional polymers are, of course, polymers having cross-links between the essentially linear polymeric structures forming the skeletal backbones of the molecules. There can be some branching within the skeletal backbones without having a departure from essential linearity.

Polyesters have been synthesized in the past from a variety of reactants through the use of several reaction schemes. The most direct synthesis is the esterification of a dicarboxylic acid with a glycol. (Dicarboxylic acids and glycols are sometimes referred to, respectively, as dibasic acids and dihydroxy compounds). In this scheme, the dicarboxylic acid/glycol mixture is heated until condensation occurs. The products of the condensation reaction are polyester and water.

Polyesters can also be prepared by ester exchange reactions.

A third general method of preparing polyesters, and the one which is most useful in the practice of the instant invention, is the polycondensation of polyols with acyl halides such as diacid chlorides. The products of this polycondensation reaction are, of course, the polyester and a hydrogen halide such as hydrogen chloride. Depending upon the physical properties of the reactants, the acyl halide-polyol reaction is frequently conducted in the presence of an inert solvent such as chlorobenzene or a chlorinated biphenyl. A stream of an inert gas is frequently passed through the reaction system to remove the gaseous hydrogen halide. It is also possible to conduct the acyl halide polyol reaction without the use of solvents if the reactants are low melting compounds which can form a homogeneous mixture. In either case, it is essential that all components of the reaction system be free of moisture since water hydrolizes the acyl halide thereby terminating the polymerization reaction.

SUMMARY OF THE INVENTION

Stable, three dimensional polyester foams are formed by reacting together acyl halides, polyols, and polyhydroxy cross-linking agents in the presence of alkali metal carbonates under such conditions as to form foams. After formation, the polyester foams can be crushed so as to rupture membranes between cells thereby producing interconnected networks of cells and to aid in the release of entraped gaseous hydrogen halide.

It is an object of the present invention to prepare stable, resilient polyester foams from acyl halides, polyols, and polyhydroxy cross-linking agents reacted in the presence of alkali metal carbonate.

It is a further object of this invention to prepare stable, resilient foam materials based on three dimensional polyesters prepared from acyl halides, polyols, and polyhydroxy cross-linking agents.

It is a still further object of this invention to prepare stable, resilient foam materials wherein the relative degrees of hydrophilicity are controlled by the nature of the reactants used to prepare the resilient foam materials.

It is a still further object of this invention to prepare absorbent, resilient polyester foam materials.

It is an object of this invention to prepare polyester foam materials which can be used in place of polyurethane foam materials. It is a further object of this invention to prepare polyester foam materials which do not produce the undesirable level of toxic gases produced when polyurethane foam materials burn.

It is a still further object of this invention to prepare stable, absorbent, resilient, polyester foam materials which are pharmacologically acceptable for use in contact with the human body.

These and other objects will become readily apparent from the Detailed Description of the Invention which follows.

DETAILED DESCRIPTION OF THE INVENTION

While this specification concludes with claims particularly pointing out and distinctly claiming the subject matter regarded as the invention, it is believed that the invention disclosed herein can be better understood from the following detailed description.

As used herein, "stable" refers to materials which retain their physical properties upon storage at ambient and near-ambient conditions for at least several weeks. As used herein, "resilient" refers to the ability of a material to essentially return to its original configuration after a deforming force is removed. As used herein, "pharmacologically acceptable" refers to the ability of a material to be used in intimate contact with portions of the human body, such as skin or mucous membrane, without producing deleterious results. Unless otherwise indicated, the terms "foam," "polyester foam," and "polyester foam material" are used interchangeably herein and refer to cellular structures the cell walls of which are formed from solid polymeric material derived from polyesters.

The polyester foam materials of the instant invention are prepared from a reaction mixture comprising four components: acyl halide, polyvol, polyhydroxy cross-linking agent, and alkali metal carbonate.

While any suitable method of preparation can be used, a preferred method for making polyester foams is similar to that used in the well-known one-shot method of preparing polyurethane foams. The various reaction components are supplied at a temperature of from about 20° to about 65° C to a mixing head wherein they are violently agitated for from about 0.005 to about 0.5 minute at a temperature of from about 20° to about 65° C and at a pressure of from about zero to about 7.03 kilograms per square centimeter (about zero to about 100 pounds per square inch). The foamed mixture is then discharged onto a moving belt. The foam is allowed to cure for from about 5 to about 1,000 minutes at a temperature of from about 20° C. to about 100° C. Curing can be accelerated through the addition of energy to the foam. The cured foam is then ready for such further processing as is dictated by the use to which the material will be put.

A very simple and effective batch method of preparation comprises mixing the polyol and the polyhydroxy cross-linking agent and heating the mixture to the desired temperature. To the above mixture, in a suitable container, is added the alkali metal carbonate with vigorous mixing. Following a mixing period, the acyl halide is added with mixing. The resulting mass, which can optionally be placed in a suitable container, is allowed to cure at ambient temperature. Infra-red radiation can optionally be used to accelerate the curing of the surface of the foam mass.

Alternatively, any two or three of the reaction components can be prereacted, in any desired proportions, and the product of this prereaction then reacted with the balance of the reaction components as indicated above.

Acyl halides (sometimes called polycarboxylic acid halides) useful in the present invention are organic compounds containing at least two -COX radicals wherein X is a halogen atom. Preferably, the acyl halides are dicarboxylic chlorides having the general formula CLOC-R-COCL wherein R is an aliphatic group defined as $(CH_2)_n$ wherein n is greater than or equal to three. Examples of preferred dicarboxylic acid chlorides are glutaryl chloride, adipyl chloride, pimelyl chloride, suberyl chloride, azelayl chloride and sebacyl chloride. The most preferred acyl halide for use in making stable, absorbent, resilient foams which can be used to absorb body fluids is the diacid chloride of adipic acid, adipyl chloride. Although in general a single acyl halide will be used, the use of mixtures of two or more acyl halides is within the scope of this invention.

Polyols are organic compounds containing a plurality of hydroxyl groups. Two different types of polyols serving two different functions are used herein. For convenience, one is referred to simply as "polyol" and the other is referred to as "polyhydroxy cross-linking agent." The distinction between the two will become readily apparent from a reading of the following paragraphs.

As used herein, "polyol" refers to an organic molecule having at least two hydroxyl groups and an equivalent weight of at least about 1,000, preferably at least 1,500. Preferably, the polyol is aliphatic. These polyols serve primarily to make up the basic skeletal structures of the polyester of this invention.

Diols (polyol compounds containing two hydroxyl groups) suitable for use in the instant invention are the ethylene oxide-propylene oxide-propylene glycol polymers such as Pluracol Polyol 686 made by BASF Wyandotte of Wyandotte, Michigan. Pluracol Polyol 686 is an ABA block copolymer containing about 80% ethylene oxide (A) and 20% propylene oxide (B). It is a diol having a molecular weight of approximately 5,000 and a hydroxyl number of 22.4 (Hydroxyl number is defined as the number of milligrams of potassium hydroxide required to completely neutralize the hydrolysis product of the fully acylated derivative prepared from one gram of polyol. Mathematically, the hydroxyl number of a compound is equal to 56,100 times the number of hydroxyl groups in the compound divided by the molecular weight of the compound.)

An example of a suitable triol (polyol compound containing three hydroxyl groups) is the liquid ethoxylated-propoxylated glycerin sold by The Dow Chemical Company of Midland, Michigan under the tradename XC1421. This material has a molecular weight of about 5,000, is about 65% ethylene oxide, and has a hydroxyl number of about 33.7.

Quadrafunctional polyols are preferred for use in the instant invention. (As used herein, "quadrafunctional" and "trifunctional" refer to compounds having, respectively, four and three hydroxyl groups available for reaction.) It has been surprisingly discovered that quadrafunctional polyols produce a polyester foam which is more resilient than that produced from other polyols. Examples of quadrafunctional polyols are ethylene oxide-propylene oxide block copolymers based on either ethylene diamine or on pentaerythritol. The former are sold under the Tetronic tradename by BASF Wyandotte. The latter, having a molecular weight from about 4,000 to about 30,000 and an ethylene oxide content of from about 5% to about 90%, are preferred for use in the instant invention in making absorbent, resilient polyester foams useful in catamenial tampons.

Polyols based on ethylene oxide without propylene oxide present can be used, but such polyols generally have a melting point too high for convenient processing. Ethylene oxide contents greater than about 60% and less than about 90% are generally preferred.

Mixtures of polyols can be used in this invention.

As used herein, "polyhydroxy cross-linking agent" refers to a propoxylated derivative (adduct) of a polyhydric alcohol. These polyhydroxy cross-linking agents contain secondary available hydroxyl groups. These propylene oxide-based materials used in the instant invention must be at least trifunctional, preferably quadrafunctional. They should have an equivalent weight of less than about 250. Preferably, they should have a molecular weight of less than about 500. Especially preferred are the propylene oxide adducts of trimethylol propane and pentaerythritol. Suitable materials are sold under the Pluracol tradename as TP340, TP440, PEP450 and PEP550 by BASF Wyandotte. TP340 is the tripropoxylated derivative of trimethylol propane while TP440 is the tetrapropoxylated derivative. PEP450 and PEP550 are the tetrapropoxylated and pentapropoxylated derivatives of pentaerythritol. Polyhydroxy cross-linking agents serve primarily to introduce covalent cross-links between essentially linear portions of the skeletal structure of the polyester foam of this invention.

Mixtures of polyhydroxy cross-linking agents as well as a single polyhydroxy cross-linking agent can be used to produce the polyester of this invention.

The alkali metal carbonates useful in the instant invention are well known inorganic compounds. Preferably, reagent grade sodium carbonate is used. It has been discovered that some samples of technical grade sodium carbonate will not function properly in this invention. However, heating these samples to about 700° C for several minutes has been found to convert them to properly functioning materials. Preferably, the alkali metal carbonate is finely ground. Particularly preferred is reagent grade sodium carbonate ground so that 100% will pass through a 400 mesh screen.

Because of the aforementioned polymerization termination action of water, the level of moisture in the total reaction system should be maintained below about 0.1% by weight.

Further, it has been found that inorganic bases, such as sodium hydroxide, do not function in the instant invention in place of the alkali metal carbonates. Among other reasons for this is the fact that they are hygroscopic and tend to introduce excessive amounts of water into the system.

As used herein, "reaction system" encompasses the total quantity of reaction components used to make the polyester foams of this invention.

Acid halide index is a measure of the amount of acid halide present in the reaction system. It is defined as 100 times the ratio of the number of acid halide equivalents present in the reaction system to the number of equivalents of available hydroxyls present in the reaction system. An acid halide index of 100 indicates the presence of stoichiometric quantities of acid halide and available hydroxyls. An acid halide index greater than 100 indicates the presence of an excess of acid halide while an acid halide index smaller than 100 indicates the presence of an excess of hydroxyls in the reaction system.

The acid halide index of the reaction system useful in the instant invention should be approximately 100. Systems having an acid halide index greater than about 98 have been found suitable. A slight excess of acyl halide (acid halide index greater than 100) is permissible and preferable. Thus reaction systems having an acid halide index smaller than about 108 but greater than about 100 are preferred. Acid halide indicies between about 98 and about 108 represent systems having a substantially stoichiometric amount of acyl halide.

The amount of acyl halide present in the reaction system has a profound effect on the density of the polyester foam produced. It has been demonstrated that when the acid halide level increases from about 19% to about 21% by weight of the reaction system, while the number of equivalents of hydroxyls present is adjusted to maintain a constant acid halide index, the density of the polyester foam decreases from about 10 pounds per cubic foot (0.16 gram per cubic centimeter) to about 4 pounds per cubic foot (0.06 gram per cubic centimeter). For use in catamenial tampons, as hereinafter described, resilient foams of low density are preferred. For other uses, of course, other densities can be more suitable.

The amount of polyhydroxy cross-linking agent present should be from about 15% to about 80% by weight of the polyol present, preferably from about 20% to about 40%.

The amount of alkali metal carbonate present should be from about 2% to about 150%, preferably from about 25% to about 67%, by weight of the total amount of polyol, polyhydroxy cross-linking agent and acyl halide present. Small quantities of alkali metal bicarbonate, such as sodium bicarbonate, are tolerated by the system. Alkali metal bicarbonate up to a level of about 5% by weight of the total organic materials present can be added without adverse effect.

Mixtures of acyl halides, polyols, and polyhydroxy cross-linking agents can be used to prepare polyester foams if one follows the general reaction scheme described in this specification. It has been discovered, however, that the foams so prepared are unstable after curing; they tend to liquify during storage at ambient conditions. It has been surprisingly discovered that the addition of alkali metal carbonate to the reaction system leads to the formation of foams having excellent stability even during prolonged storage. It has also been discovered that low levels of alkali metal bicarbonate in the absence of alkali metal carbonate improve the stability of polyester foams over that of foams made without the inclusion of either alkali metal carbonate or bicarbonate in the reaction mixture, but the improvement in polyester foam stability engendered by alkali metal bicarbonate is significantly less than that engendered by alkali metal carbonate.

Without advancing a specific theory as to the function of the alkali metal carbonate, it can be stated that this material neither appears to enter into the reaction as by becoming a part of the polymer structure nor appears to function as a blowing agent. Essentially all the alkali metal carbonate can be recovered after the polymerization reaction is complete.

The hydrophilic/hydrophobic character of the polyester foams of this invention is determined in large part by the nature of the reactants from which the polyester is formed. For example, when propoxylated - ethoxylated pentaerythritol having a molecular weight of more than 15,000 and an ethylene oxide content greater than 70% is used as the polyol, the resulting polyester is hydrophilic whereas that made with a similar polyol having an propylene oxide content of about 90% by weight in hydrophobic. Also, increasing the length of the aliphatic chain in the acyl halide, as by changing from glutaryl chloride to adipyl chloride, decreases the hydrophilicity of the resulting polyester foam. It is well within the ability of the skilled artisan having before him the teachings of this specification to select reactants that will yield a polyester foam material with the hydrophilic/hydrophobic character best suited for the use at hand.

In addition to the four required components of the reaction mixture, additional materials can be present so long as their presence does not interfere with the fundamental polycondensation reaction. Examples of optional materials include nonionic surfactants useful as uncured foam stabilizers, catalytic surfactants, pigments, flame retardant chemicals, and the like. Pluronic L-92, a nonionic surfactant having a molecular weight of about 3,600 and a hydroxyl number of about 31, as made by BASF Wyandotte, is particularly useful as a catalytic surfactant. (Catalytic surfactants contribute to the structure of polyester, and polyurethane, foams by reducing foam cell size and promoting uniform foam cell size.)

In order to more fully describe the present invention, and not by way of limitation, the following examples are presented.

EXAMPLE I

A mixture consisting of 400 grams Pluracol Polyol 686 (polyol) and 144 grams Pluracol TP-340 (polyhydroxy cross-linking agent) was heated in a stainless steel vessel to a temperature of 40° C. This mixture also contained 0.1 gram Pluronic L-92 (catalytic surfactant). The heated mixture was transferred to a cylindrical paper container 8.9 centimeters in diameter. To the mixture in the cylindrical paper container was added 100 grams sodium carbonate of which 100% would pass through an 80 mesh screen and 50% would pass through a 200 mesh screen. The resulting mixture was agitated for 25 seconds with a 6.1 centimeter diameter turbine blade mixer. At the end of the initial mixing, 151 grams adipyl chloride was added and the total reaction composition was agitated for an additional 10 seconds. The resulting resilient polyester foam was removed from the cylindrical paper container and subjected to infra-red radiation to hasten the curing of the surface. The resulting resilient polyester foam had a density of 0.045 grams per cubic centimeter.

EXAMPLE II

A mixture consisting of 397.6 grams Dow XD 1421 (polyol) and 192.4 grams Pluracol TP-440 (polyhydroxy cross-linking agent) was placed in a stainless steel vessel. Four grams Pluronic L-92 (catalytic surfactant) were also added to the mixture. The procedure of Example I was followed in making a resilient polyester foam except that the initial mixture was heated to 45° C. The quantity of sodium carbonate used in this example was 200 grams while 155 grams adipyl chloride was used. The resulting resilient polyester foam had a density of 0.06 grams per cubic centimeter.

EXAMPLE III

The absorbent, resilient polyester foam made in this example was based on a polyol which was an ethylene oxide-propylene oxide block copolymer of pentaerythritol and which had an ethylene oxide content of 73% and a hydroxyl number of 14. A mixture consisting of 199.9 grams of the aforementioned polyol and 73.1 grams Pluracol PEP-450 (polyhydroxy cross-linking agent) plus 2 grams Pluronic L-92 (catalytic surfactant) was placed in a stainless steel vessel and heated to 50° C. The warmed mixture was transferred to a paper cylinder 8.9 centimeters in diameter. To the mixture in the paper cylinder was added 100 grams sodium carbonate as used in Example I and the system was agitated for 20 seconds with a 7.6 centimeter diameter six-bladed mixer. Following the initial mixing, 74 grams adipyl chloride was added to the system and mixing was continued for 10 seconds. The total reaction system was poured into a 15.2 centimeter by 22.9 centimeter rectangular container and allowed to set. After the surface of the polyester foam had been subjected to infrared radiation for 5 minutes to reduce surface tackiness, the foam mass was crushed between opposing rollers. The resulting absorbent, resilient, open celled polyester foam had a density of 0.06 gram per cubic centimeter. After comminuting and washing with water, the absorbent, flexible polyester foam of this example was eminently suitable for use in the catamenial aggregate absorbent body described by Schaefer in U.S. Pat. No. 3,815,601.

For some applications, it is desirable that the polyester foam be open celled. As used herein, the term "open celled" means that the individual cells of the foam are interconnected by open channels. Cured polyester foam can be converted to the open celled state by subjecting it to sufficient compressive force to reduce its volume to about 20% of its original value. This compression tends to rupture the membranes making up the individual cell walls. In addition to forming an interconnected network of channels and cells, this compression and the resulting membrane rupture facilitates the release of gaseous hydrogen halide from the cured foam mass.

For use in catamenial tampons, it is preferred that the polyester foam be open celled and have from about 50 to about 400 cells per linear inch.

For some applications, it is desirable that the residual alkali metal carbonate and hydrogen halide be washed from the polyester foam mass. This washing can be readily accomplished by reducing the foam mass to convenient sized particles (as by chopping or cutting) and agitating these particles in a suitable solvent such as water. In most cases, the residual alkali metal carbonate is more than sufficient to neutralize any residual hydrogen halide present. Following washing, the polyester foam can be dried in any convenient, known manner that will be readily apparent to those skilled in the art.

The novel polyester foams of the instant invention find application in numerous circumstances where soft, resilient, absorbent foam materials are required. For example, the comminuted and washed foam of the instant invention can be used in the catamenial aggregate absorbent body described by Schaefer in U.S. Pat. No. 3,815,601 which was issued on June 11, 1974, and which is incorporated herein by reference.

Further, the novel polyester foams of the instant invention can be used in applications where polyurethane foams are now used. Such applications include use in surgical bandages, household sponges, furniture pads, and the like.

EXAMPLE IV

In this example, portions of two of the reaction components are prereacted and the prereaction product is used in the formation of a polyester foam of this invention.

One hundred fifty grams Pluralcol PEP-450 (polyhydroxy cross-linking agent) was mixed with 35.7 grams adipyl chloride (96% purity) for 20 seconds at room temperature and atmospheric pressure in a 500 milliliter beaker with a 7.6 centimeter diameter turbine blade mixer. The resulting product was allowed to degas for one hour at room temperature. A 105.7 gram aliquot of the reaction product was mixed with 250 grams Pluracol Polyol 747 and 2.5 grams Pluronic L-92. Pluracol Polyol 747 is an ethylene oxide-propylene oxide block copolymer of pentaerythritol, has an ethylene oxide content of 73% and a hydroxyl number of 14, and is manufactured by BASF Wyandotte. A 286.6 gram aliquot of this last described mixture, which had been heated to 50° C in a steel beaker, was mixed with 100 grams anhydrous, reagent grade sodium carbonate for 20 seconds in a 0.95 liter cylindrical paper can with the hereinbefore described mixer. To the mixture in the cylindical paper can, 57.9 grams adipyl chloride (96% purity) was added and mixed for 10 seconds. The resulting product exhibited a cream time of 30 seconds and a rise time of 1 minute 50 seconds.

After being allowed to cure for 5 minutes at room temperature, the resulting polyester foam was open celled (i.e. required no reticulation to produce open cells) and had an exceedingly fine cell structure. It had a density of approximately 0.19 grams per cubic centimeter (11.7 pounds per cubic foot).

What is claimed is:

1. A stable, resilient polyester foam comprising a three-dimensional condensate of:

(a) at least one polyol having at least two hydroxyl groups and an equivalent weight of at least about 1,000;

(b) at least one propylene oxide-based polyhydroxy cross-linking agent having at least three hydroxyl groups and an equivalent weight of less than about 250 said equivalent weight based hydroxy groups; and (c) at least one acyl halide having at least two —COX radicals wherein X is a halogen atom.

2. A stable, resilient polyester foam comprising a three-dimensional condensate of:

(a) at least one polyol having at least two hydroxyl groups and an equivalent weight of at least about 1,000;

(b) at least one propylene oxide-based polyhydroxy cross-linking agent having at least three hydroxyl groups and a molecular weight of less than about 500; and (c) at least one acyl halide having at least two —COX radicals wherein X is a halogen atom.

3. A polyester foam according to claim 2 which comprises:

(a) one part by weight of polyol;

(b) from about 0.15 part by weight to about 0.80 part by weight of polyhydroxy cross-linking agent; and (c) a substantially stoichiometric amount of acyl halide.

4. A hydrophilic polyester foam according to claim 3 wherein the polyol is an ethylene oxide-propylene oxide polymer and is characterized by an ethylene oxide content of at least about 60% by weight.

5. A foam according to claim 4 wherein the polyol is quadrafunctional.

6. A foam according to claim 5 wherein the quadrafunctional polyol is an ethylene oxide-propylene oxide polymer based on pentaerythritol.

7. A foam according to claim 4 wherein the polyhydroxy cross-linking agent is quadrafunctional.

8. A foam according to claim 7 wherein the quadrafunctional polyhydroxy cross-linking agent is a propylene oxide adduct of pentaerythritol.

9. A stable, resilient, hydrophilic polyester foam according to claim 3, comprising a three-dimensional condensate wherein (a) the polyol is a quadrafunctional ethylene oxide-propylene oxide block copolymer of pentaerythritol and is characterized by an ethylene oxide content of at least about 60% by weight and a molecular weight of at least about 4,000;

(b) the polyhydroxy cross-linking agent is a quadrafunctional propylene oxide adduct of pentaerythritol; and (c) the acyl halide is adipyl chloride.

10. A pharmacologically acceptable foam according to claim 9 which is substantially open celled.

11. A foam according to claim 10 wherein the open-celled foam is characterized by from about 50 to about 400 cells per linear inch.

12. A foam according to claim 11 which is especially adapted for absorbing body fluids and which is characterized by a density of about 0.06 grams per cubic centimeter.

13. A hydrophobic polyester foam according to claim 3 wherein the polyol is an ethylene oxide-propylene oxide polymer and is characterized by a propylene oxide content of at least about 60% by weight.

14. A foam according to claim 13 wherein the polyol is quadrafunctional.

15. A foam according to claim 14 wherein the quadrafunctional polyol is an ethylene oxide-propylene oxide polymer based on pentaerythritol.

16. A foam according to claim 13 wherein the polyhydroxy cross-linking agent is quadrafunctional.

17. A foam according to claim 16 wherein the quadrafunctional polyhydroxy cross-linking agent is a propylene oxide adduct of pentaerythritol.

18. A process for making a stable, resilient polyester foam comprising reacting:

(a) at least one polyol having at least two hydroxyl groups and an equivalent weight of at least about 1,000;

(b) at least one propylene oxide-based polyhydroxy cross-linking agent having at least three hydroxyl groups and an equivalent weight of less than about 250; and (c) at least one acyl halide having at least two —COX radicals wherein X is a halogen atom;

in the presence of alkali metal carbonate.

19. The process of claim 18 wherein at least a portion of said polyhydroxy cross-linking agent is prereacted with at least a portion of said acyl halide.

20. A process for making a stable, resilient polyester foam comprising reacting:

(a) at least one polyol having at least two hydroxyl groups and an equivalent weight of at least about 1,000;

(b) at least one propylene oxide-based polyhydroxy cross-linking agent having at least three hydroxyl groups and a molecular weight of less than about 500; and (c) at least one acyl halide having at least two —COX radicals wherein X is a halogen atom;

in the presence of alkali metal carbonate.

21. The process of claim 20 wherein there is reacted:

(a) one part by weight of polyol;

(b) from about 0.15 part by weight to about 0.80 part by weight of polyhydroxy cross-linking agent; and (c) a substantially stoichiometric amount of acyl halide;

and wherein there is present an amount of alkali metal carbonate equal to from about 2% to about 150% by weight of the total amount of polyol, polyhydroxy cross-linking agent and acyl halide present.

22. The process of claim 21 wherein the polyol is an ethylene oxide-propylene oxide polymer and is characterized by an ethylene oxide content of at least about 60% by weight.

23. The process of claim 22 wherein the polyol is quadrafunctional.

24. The process of claim 23 wherein the quadrafunctional polyol is an ethylene oxide-propylene oxide polymer based on pentaerythritol.

25. The process of claim 22 wherein the polyhydroxy cross-linking agent is quadrafunctional.

26. The process of claim 25 wherein the quadrafunctional polyhydroxy cross-linking agent is a propylene oxide adduct of pentaerythritol.

27. The process of claim 21 wherein:

(a) the polyol is a quadrafunctional ethylene oxide-propylene oxide block copolymer of pentaerythritol and is characterized by an ethylene oxide content of at least about 60% by weight and a molecular weight of at least about 4,000;

(b) the polyhydroxy cross-linking agent is a quadrafunctional propylene oxide adduct of pentaerythritol; and
(c) the acyl halide is adipyl chloride.

28. The process of claim 27 which includes the additional steps of curing the foam and compressing the cured foam to about 20% of its original volume.

29. The process of claim 20 which includes the additional steps of curing the foam and compressing the cured foam to about 20% of its original volume.

30. The process of claim 20 wherein at least a portion of said polyhydroxy cross-linking agent is prereacted with at least a portion of said acyl halide.

* * * * *